United States Patent [19]

Morita et al.

[11] Patent Number: 5,153,198
[45] Date of Patent: Oct. 6, 1992

[54] AGENT FOR TREATMENT OF DISORDERS OF THE CEREBRO-NEURAL TRANSMISSION SYSTEM

[75] Inventors: Takakazu Morita, Toyonaka; Tadashi Iso, Kawachinagano; Hideyasu Yamauchi, Nagaokakyo, all of Japan

[73] Assignee: Santen Pharmaceutical Co., Ltd., Osaka, Japan

[21] Appl. No.: 780,818

[22] Filed: Oct. 23, 1991

Related U.S. Application Data

[62] Division of Ser. No. 486,542, Feb. 28, 1990, Pat. No. 5,087,627.

[30] Foreign Application Priority Data

Mar. 15, 1989 [JP] Japan ................. 1-64148

[51] Int. Cl.⁵ .................. A61K 31/495; C07D 295/00
[52] U.S. Cl. .................. 514/255; 544/377; 544/398; 544/403
[58] Field of Search .................. 544/377, 398, 403; 514/255

[56] References Cited

U.S. PATENT DOCUMENTS

| | | | |
|---|---|---|---|
| 3,957,788 | 5/1976 | Nishimura et al. | 514/255 |
| 4,265,894 | 5/1981 | Gootjes et al. | 544/391 |
| 4,656,175 | 4/1987 | Bjork et al. | 514/255 |
| 4,757,074 | 7/1988 | Coker et al. | 514/255 |

FOREIGN PATENT DOCUMENTS

| | | |
|---|---|---|
| 490372 | 9/1975 | Australia . |
| 49-00188 | 1/1974 | Japan . |
| 2007976 | 1/1977 | Japan . |
| 2039687 | 3/1977 | Japan . |
| 63-141966 | 6/1988 | Japan . |
| 863180 | 3/1961 | United Kingdom . |

OTHER PUBLICATIONS

Nishimura et al., Chemical Abstract, 109579j, vol. 89, (1978), p. 932.

Iwao et al., Chemical Abstract, 149568t, vol. 109, (1988), p. 742.

R. P. Shank et al., "Preclinical Evaluation of McN-5707 as a Potential Antidepressant", J. Pharm. Exp. Ther., vol. 242, No. 1, pp. 74–84.

C. Idzikowski et al., "5-Hydroxytryptamine-2 Antagonist Increases Human Slow Wave Sleep", Brain Research, 378, (1986), pp. 164–168.

Irwin Lucki et al., "Differential Actions of Serotonin Antagonists on Two Behavioral Models of Serotonin Receptor Activation in the Rat", J. Pharm. Exp. Ther., vol. 228, (1984), pp. 133–139.

*Primary Examiner*—Cecilia Tsang
*Attorney, Agent, or Firm*—Frishauf, Holtz, Goodman & Woodward

[57] ABSTRACT

A compound of the formula [II] or pharmaceutically acceptable salt thereof,

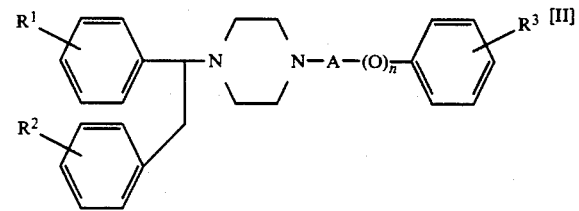

wherein
$R^1$ is hydrogen or fluorine;
$R^2$ is hydrogen or fluorine;
$R^3$ is hydrogen, lower alkyl, lower alkoxy, halogen or lower alkylenedioxy;
A is straight or branched lower alkylene having 1 to 6 carbon atoms; and n is 0 or 1, provided that at least one of $R^1$ or $R^2$ is fluorine. Such compound is useful for treatment of disorders of the cerebro-neural transmission system.

19 Claims, No Drawings

AGENT FOR TREATMENT OF DISORDERS OF THE CEREBRO-NEURAL TRANSMISSION SYSTEM

This application is a divisional application of U.S. application Ser. No. '07/486,521, filed Feb. 28, 1990, now U.S. Pat. No. 5,087,627.

BACKGROUND OF THE INVENTION

Diphenylethylamine derivatives were well recognized analgesic (Japanese Patent Publication 24084/1961 etc.) and especially (−)-N,N-dimethyl-1,2-diphenylethylamine, lefetamine, is known to have an excellent analgesic effect.

Chemical modification of amine moiety was also studied, and diphenylethylpiperazine derivatives were reported in Japanese Patent Publication 33827/1986 to have an analgesic effect. Furthermore, we reported that diphenylethylpiperazine derivatives had a calcium antagonistic effect (Japanese Unexamined Patent Publication 141966/1988). Diphenylethylpiperazine derivatives were already known to have analgesic effect and calcium antagonistic effect, but the other useful pharmacological properties were not known.

DETAILED DESCRIPTION OF THE INVENTION

This invention relates to:

1) an agent, having the chemical formula [I] or salts thereof which includes novel compounds as well as known compounds, for treatment of disorders of cerebro-neural transmission system,

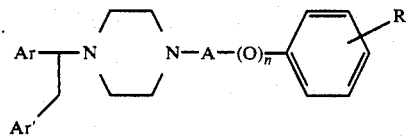

[I]

wherein
Ar or Ar' is phenyl or pyridyl, which can be substituted by lower alkyl, lower alkoxy, halogen or lower alkylenedioxy;
R is hydrogen, lower alkyl, lower alkoxy, halogen or lower alkylenedioxy;
A is straight or branched alkylene having 1 to 6 carbon atoms; and
n is 0 or 1, 2) novel fluor-compounds of the formula [II] or salts thereof which are useful for treatment of disorders of cerebro-neural transmission system,

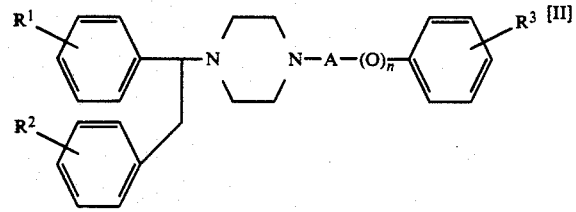

[II]

wherein
$R^1$ is hydrogen or fluorine;
$R^2$ is hydrogen or fluorine;
$R^3$ is hydrogen, lower alkyl, lower alkoxy, halogen or lower alkylenedioxy;
A is straight or branched lower alkylene having 1 to 6 carbon atoms; and n is 0 or 1,
provided that at least one of $R^1$ or $R^2$ is fluorine.

The terms defined above are explained as follows in more detail.

The term "lower alkyl" intends to designate straight or branched alkyl having 1 to 6 carbon atoms exemplified by methyl, ethyl, propyl, isopropyl, butyl and hexyl. The term "lower alkoxy" intends to designate straight or branched alkoxy having 1 to 6 carbon atoms exemplified by methoxy, ethoxy, propoxy, isopropoxy, butoxy and hexyloxy. The term "lower alkylenedioxy" intends to designate alkylenedioxy having 1 to 3 carbon atoms exemplified by methylenedioxy and ethylenedioxy. The term "halogen" intends to designate fluorine, chlorine, bromine and iodine. The substituent of phenyl or pyridyl group can be one or more. When the group has plural substituents, the substituents can be the same or different.

The "salt" means a pharmaceutically acceptable salt such as hydrochloric acid salt, sulfuric acid salt, phosphoric acid salt, lactic acid salt, maleic acid salt and oxalic acid salt.

Hereinafter, the compound represented by the formula [I] is referred to as the "Compound" and the compound of the formula [II] is referred to as the "Fluor-Compound".

The Fluor-Compound is a novel compound which has not been disclosed in any prior arts. The definition of the Fluor-Compound is different from that of the Compound, but the Fluor-Compound is included in the scope of the Compound.

Synthetic methods of the Compound are shown below,

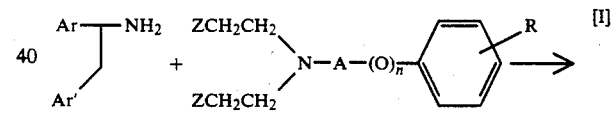

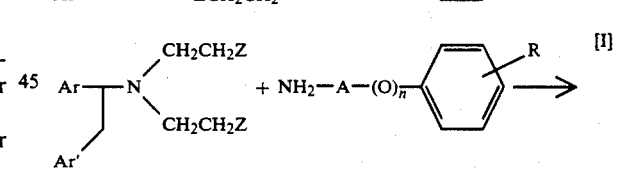

wherein Z is hydrogen or methanesulfonyl.

The Compound has optical- or stereoisomer because of the existence of one or more asymmetric carbon atoms, and the isomer is included in this invention.

As mentioned before, piperazine derivatives were known to have analgesic effect and calcium antagonistic effect. We studied the known piperazine derivatives for their new pharmacological effects. Furthermore, we synthesized novel compounds, namely Fluor-Compound, and studied their pharmacological effects.

As the result of our study, we found that the Compound has an excellent improvement effect on disorders of cerebro-neural transmission system. Particularly, the Fluor-Compound improved defects of memory very excellently.

As the disorders of cerebro-neural transmission system, many kinds of defects of memory, insomnia, depression, schizophrenia etc. are known. Medicinal substances which improve such disorders are useful for treatment or prevention of senile dementia such as Alzheimer's disease and dementia caused by disorders of cerebral vessels, dementia caused by Parkinson disease or head injuries, etc., insomnia, depression or schizophrenia, etc.

As examples of the studies to examine improvable effects on disorders of cerebro-neural transmission system, one-trial passive avoidance test in mice and antagonistic test against 5-hydroxytryptamine (serotonine, hereinafter referred to as 5-HT) using vessels of rabbits were disclosed. 5-HT has various actions on the central nervous system and the existence of two types of 5-HT receptor, namely type 1 and type 2, was reported (hereinafter type 2 receptor is referred to as 5-HT$_2$).

It is reported that medical substance showing 5-HT$_2$ antagonistic effect has improves defect of memory (Pharmacol. Biochem. Behav., 28, 353-359 (1987)), insomnia (Brain Res., 378, 164-168 (1986)), depression (Science, 210, 88-90, (1980)), or psychopathia (J. Pharmacol. Exp. Ther., 228, 133-139, (1984) and J. Pharm. Soc. Jap., 106, 351-370 (1986)).

Therefore, 5-HT$_2$ antagonist is effective on various kinds of disorders of cerebro-neural transmission system. The Compound showed excellent effect in the above mentioned tests. The details are explained in the part of pharmacological test.

Especially, the Fluor-Compound, even in a low dosage, showed an excellent effect in the one-trial passive avoidance test with higher efficacy than the known compounds. This suggests that the Fluor-Compound would be useful for treatment of dementia.

The Compound can be administered either orally or parenterally. Examples of the dosage forms are tablet, capsule, granules, powder, suppository and injection. The dosage is adjusted depending on symptom, dosage form, etc., but usual daily dosage is 1 to 1000 mg in one or a few divided doses.

PHARMACOLOGICAL TEST

As examples of pharmacological tests, one-trial passive avoidance test in mice (pharmacological test 1) and antagonistic test against 5-HT$_2$ using vessel of rabbit (pharmacological test 2) were shown.

Novel Fluor-Compound, which has not been disclosed in any prior arts, and the known compounds disclosed in Japanese Unexamined Patent Publication 141966/1988 and optical isomers thereof were tested. Examples of the compounds tested are shown as below.

(±)-1-[1,2-Bis(4-fluorophenyl)]ethyl-4-[2-(3,4-dimethoxyphenyl)ethyl]piperazine dihydrochloride (compound No.1) mp 265°-267° C. (dec.)

(±)-1-[1-(4-Fluorophenyl)-2-phenyl]ethyl-4-[2-(3,4-dimethoxyphenyl)ethyl]piperazine dihydrochloride (compound No.2) mp 263° C. (dec.)

(±)-1-[2-(4-Fluorophenyl)-1-phenyl]ethyl-4-[2-(3,4-dimethoxyphenyl)ethyl]piperazine dihydrochloride (compound No.3) mp 264° C. (dec.)

(±)-1-(1,2-Diphenyl)ethyl-4-[2-(3,4-dimethoxyphenyl)ethyl]piperazine dihydrochloride (compound No.4) mp 251°-254° C. (dec.)

(−)-1-(1,2-Diphenyl)ethyl-4-[2-(3,4-dimethoxyphenyl)ethyl]piperazine dihydrochloride (compound No.5) mp 225°-230° C. (dec.)

(+)-1-(1,2-Diphenyl)ethyl-4-[2-(3,4-dimethoxyphenyl)ethyl]piperazine dihydrochloride (compound No.6) mp 225°-230° C. (dec.)

(±)-1-(1,2-Diphenyl)ethyl-4-[2-(3,4-methylenedioxyphenoxy)ethyl]piperazine dihydrochloride (compound No.7) mp 242°-243° C. (dec.)

(±)-1-[2-Phenyl-1-(4-pyridyl)ethyl]-4-[2-(3,4-dimethoxyphenyl)ethyl]piperazine dioxalate (compound No.8) mp 168°-171° C. (dec.)

(±)-1-[(2-Phenyl)-1-(3-pyridyl)ethyl]-4-[2-(3,4-methylenedioxyphenoxy)ethyl]piperazine dioxalate (compound No.9) mp 172°-175° C. (dec.)

(±)-1-[1,2-Bis(4-fluorophenyl)]ethyl-4-[2-[(3,4-methylenedioxy)phenoxy]ethyl]piperazine dihydrochloride (compound No.10) mp 246°-247° C. (dec.)

(−)-1-[1,2-Bis(4-fluorophenyl)]ethyl-4-[2-(3,4-dimethoxyphenyl)ethyl]piperazine dihydrochloride (compound No.11) mp 266°-267° C. (dec.)

(+)-1-[1,2-Bis(4-fluorophenyl)]ethyl-4-[2-(3,4-dimethoxyphenyl)ethyl]piperazine dihydrochloride (compound No.12) mp 266°-267° C. (dec.)

Pharmacological Test 1

As an experimental method to examine an efficacy of a medicinal substance on dementia, one-trial passive avoidance test is well known (Jarvic and Essman, Psychol. Rep., 6,290 (1960)).

Experimental Method

In the training session, each mouse was gently placed onto the wooden platform (4×4×4 cm) set in the center of the grid floor (21×21 cm). When the mouse stepped down from the platform and placed all its paws on the grid floor, the intermittent electric shocks (1 Hz, 0.5 sec, 60 VDC) were delivered. The step-down latency was measured, and the animals exhibiting a step-down latency ranging from 3 to 15 sec were used for the retention test.

Twenty-four hours after training, each mouse was placed on the platform again, and the step-down latency was recorded up to a maximum cut off time of 300 sec. Impairment of memory was induced by cycloheximide (CXM, protein synthesis inhibitor) or p-chloramphetamine (PCA, a release of 5-HT). CXM (60 mg/kg) dissolved in 0.9% saline was injected s.c. immediately after training session. On the other hand, PCA (5 mg/kg) dissolved in 0.9% saline was injected i.p. 30 min before training session. The test compound was suspended, in 1.0% methylcellulose and administered p.o. immediately after training session.

Normal mice were given 0.9% saline (s.c. or i.p.) and 1.0% methylcellulose (p.o.) in a volume of 0.1 ml/10 g body weight.

Control mice were given CXM or PCA alone.

Result

The experimental results are shown in Table 1 and 2.

TABLE 1

| PCA - induced amnesia model | | |
|---|---|---|
| | dose (mg/kg) | step-down latency (median, sec.) |
| normal | | 250.7 |
| control | 1.25 | 160.1 |
| compound No. 1 | | 263.6 |
| normal | | 176.1 |
| control | 10.0 | 18.6 |
| compound No. 1 | | 130.1 |
| normal | | 271.8 |
| control | 2.5 | 52.7 |
| compound No. 2 | | 199.9 |
| normal | 2.5 | 271.8 |

TABLE 1-continued

PCA - induced amnesia model

| | dose (mg/kg) | step-down latency (median, sec.) |
|---|---|---|
| control | | 52.7 |
| compound No. 3 | | 198.2 |
| normal | 10.0 | 176.1 |
| control | | 18.6 |
| compound No. 4 | | 184.7 |
| normal | 5.0 | 203.1 |
| control | | 35.0 |
| compound No. 7 | | 155.1 |
| normal | 1.25 | 203.1 |
| control | | 35.0 |
| compound No. 10 | | 206.3 |
| normal | 2.5 | 165.1 |
| control | | 43.6 |
| compound No. 11 | | 153.1 |
| normal | 2.5 | 165.1 |
| control | | 43.6 |
| compound No. 12 | | 132.0 |

TABLE 2

CXM - induced amnesia model

| | dose (mg/kg) | step-down latency (median, sec.) |
|---|---|---|
| normal | 40.0 | 225.4 |
| control | | 25.3 |
| compound No. 4 | | 77.7 |
| normal | 20.0 | 300.0 |
| control | | 21.9 |
| compound No. 5 | | 60.0 |
| normal | 20.0 | 224.1 |
| control | | 23.6 |
| compound No. 6 | | 115.4 |
| normal | 20.0 | 215.6 |
| control | | 32.6 |
| compound No. 7 | | 123.9 |

As shown in the tables, the reduction of step-down latency in control group was improved by all the compounds tested. Particularly, the group receiving the Fluor-Compound recovered its latency time to the same level or almost same level to the normal group. Furthermore, the Fluor-Compound showed very high efficacy at low doses, namely 1.25 or 2.5 mg/kg.

The result proved that the Compound can be useful for treatment of dementia.

Pharmacological Test 2

It is reported that a medicinal substance having 5-$HT_2$ antagonistic effect improves various kinds of cerebro-neural transmission system. The effect comes from the action of such substance on 5-$HT_2$ receptor in brain. It is reported that 5-$HT_2$ antagonistic effect of the medical substance on smooth muscle of vessel is correlating to the binding ability with 5-$HT_2$ receptor in brain (Leysen, J. E. et al., Molecular Pharmacology, 21, 301-314 (1982)). Therefore, in this test, the efficacy of the Compound was examined using thoracic aorta of rabbit.

Experimental Method

Japanese white rabbits were sacrificed by cervical fracture and exsanguinated. Thoracic aortas were excised rapidly. The isolated arteries were helically cut into strips, approximately 3 mm wide, and suspended in 20 ml organ bath chambers containing Krebs-Henseleit solution. Resting tensions of aortas were maintained at 1.5 g. The organ bath chambers were maintained at 37° C. and aerated continuously with 95% $O_2$-5% $CO_2$.

After equilibration, 5-HT ($10^{-6}$M) was added into each organ bath chamber. After the 5-HT-induced contraction was ascertained to be constant and reproducible, each test compound were added and 30 minutes after 5 HT was added again, and their effect on 5-HT-induced contraction was examined.

The contraction was measured with various concentrations of the test compound. According to the difference between the contraction caused by pre-treatment with the test compound and by 5-HT alone, the concentration which can inhibit 50% of the contraction caused by 5-HT alone was calculated ($IC_{50}$).

Result

The experimental results were shown in the Table 3.

TABLE 3

| test compound (compound No.) | $IC_{50}$ (M) |
|---|---|
| 1 | $2.7 \times 10^{-7}$ |
| 2 | $3.4 \times 10^{-7}$ |
| 3 | $6.4 \times 10^{-7}$ |
| 4 | $2.8 \times 10^{-7}$ |
| 5 | $2.1 \times 10^{-7}$ |
| 6 | $2.0 \times 10^{-6}$ |
| 7 | $2.7 \times 10^{-6}$ |
| 8 | $7.0 \times 10^{-6}$ |
| 9 | $4.8 \times 10^{-6}$ |
| 10 | $2.1 \times 10^{-6}$ |
| 11 | $2.0 \times 10^{-7}$ |

As shown in the table, the Compound shows excellent inhibition of the contraction caused by 5-HT. The results confirms the excellent 5-$HT_2$ antagonistic effect of the Compound because the contraction of smooth muscle of vessel is relating to 5-$HT_2$ receptor.

EXAMPLE

Synthesis of novel Fluor-Compound are shown below.

Preparation of the intermediate

1.

N,N-Bis(2-chloroethyl)-2-(3,4-dimethoxyphenyl)ethylamine hydrochloride 2-(3,4-Dimethoxyphenyl)ethylamine (80.0 g), 2-bromoethanol (182 g) and potassium carbonate (201 g) were added to ethanol (1) and the mixture was refluxed for 16 hours. After cooling, the mixture was filtered and the filtrate was concentrated in vacuo. The oily residue was dissolved in chloroform. The solution was washed with saturated sodium chloride solution, dried over anhydrous magnesium sulfate and concentrated in vacuo to give 104.5 g(88% ) of N,N-bis(2-hydroxyethyl)-2-(3,4-dimethoxyphenyl)ethylamine in oily form.

The amine compound (104 g) was dissolved in chloroform (500 ml). To the solution, thionyl chloride (138 g) was added dropwise under ice-cooling. After the addition, the reaction mixture was refluxed for 45 minutes with stirring. After cooling, the reaction mixture was concentrated in vacuo. To the oily residue, isopropanol was added and separated crystals were collected by filtration to give 88.9 g (67.2%) of the titled compound.

mp 145°-148° C. (dec.).

IR (KBr, cm$^-$) 2920, 2380, 1590, 1509, 1450, 1262, 1237, 1158, 1139, 1025, 979.

Following compound was prepared by the similar method as in the above.

N,N-Bis(2-chloroethyl)-2-[(3,4-methylenedioxy)-phenoxy]ethylamine hydrochloride

IR (film, cm$^{-1}$) 3376, 2972, 2388, 1609, 1488, 1270, 1184, 1130, 1038, 952, 817.

2. (±)-1,2-Bis(4-fluorophenyl)ethylamine hydrochloride

A mixture of 1,2-bis(4-fluorophenyl)-1-oxoethane (2.13 g) and ammonium formate (3.78 g) was stirred for 10 hours at 190° C. After cooling, concentrated hydrochloric acid (12 ml) was added to the reaction mixture and the mixture was refluxed for 5 hours. After cooling, aqueous sodium hydroxide solution was added to the mixture and alkalized. The product was extracted with ethyl acetate and the organic layer was washed with saturated sodium chloride solution. The organic layer was dried over anhydrous magnesium sulfate and concentrated in vacuo. The oily residue was dissolved in methanol. To the solution, HCl/methanol was added and the solution was concentrated in vacuo. Separated crystals were collected by filtration to give 1.77 g (65.6%) of the titled compound.

mp 238°–240° C. (ethanol—ether).

IR (KBr, cm$^{-1}$) 3384, 2924, 1601, 1508, 1438, 1258, 1229, 1154, 1020, 835, 820.

Following compounds were prepared by the similar method as in the above.

(±)-1-(4-Fluorophenyl)-2-phenylethylamine hydrochloride mp 266°–268° C. (methanol-ether).

IR (KBr, cm$^{-1}$) 3480, 2860, 1605, 1515, 1233, 835, 749, 697

(±)-2-(4-Fluorophenyl)-1-phenylethylamine hydrochloride mp 257°–259° C. (dec.), (methanol—ether)

IR (KBr, cm$^{-1}$) 3412, 2892, 1600, 1512, 1227, 835, 699

3. (−)-1,2-Bis(4-fluorophenyl)ethylamine ½(+)-tartrate (1) and (+)-1,2-Bis(4-fluorophenyl)ethylamine ½(−)-tartrate (2)

To (±)-1,2-bis(4-fluorophenyl)ethylamine (4.67 g, prepared by treatment of the hydrochloric acid salt with potassium carbonate) dissolved in ethanol (20 ml), (+)-tartaric acid (1.50 g) was added and the mixture was warmed to be solution. Water (200 ml) was added to the solution and the mixture was warmed again to be homogeneous solution. The solution was stirred for one night at room temperature and separated crystals were collected by filtration. The crude crystals were recrystallized with water to give 1.12 g (36%) of the titled compound(1).

mp 221°–222° C. (dec.), (water).

IR (KBr, cm$^{-1}$) 3424, 2896, 1608, 1560, 1511, 1344, 1228, 1067, 845, 819.

$[\alpha]_D^{25} -66.3°$ (c=1.0, methanol).

To the filtrate removed the crude crystals of the titled compound(1), potassium carbonate was added and alkalized. From the mixture, (+)-rich amine compound (2.40 g) was obtained by extraction with ethyl acetate. (−)-Tartaric acid (0.75 g) was added to ethanol (10 ml) solution of (+)-rich amine compound and the mixture was warmed to be solution. Water(100 ml) was added to the solution and the mixture was stirred for one night at room temperature and separated crystals were collected by filtration to give 1.27 g (41%) of the titled compound(2).

mp 223° C. (dec.),(water).

IR (KBr, cm$^{-1}$) 3424, 2892, 1608, 1559, 1510, 1345, 1228, 1607, 845, 819.

$[\alpha]_D^{25} +69.3°$ (c=1.0, methanol).

The following compounds were prepared by a similar method as in the above.

(−)-1-(4-Fluorophenyl)-2-phenylethylamine ½(−)-tartrate mp 223° C. (dec.), (water).

IR (KBr, cm$^{-1}$) 3424, 2892, 1608, 1559, 1516, 1343, 1225, 1067, 845, 748, 694.

$[\alpha]_D^{25} -68.1°$ (c=0.3, methanol.

(+)-1-(4-Fluorophenyl)-2-phenylethylamine ½(−)-tartrate mp 221°–222° C. (dec.), (water).

IR (KBr, cm$^{-1}$) 3424, 2892, 1606, 1557, 1515, 1343, 1226, 1068, 846, 748, 694

$[\alpha]_D^{25} 30\ 65.5°$ (c=0.3, methanol).

(−)-2-(4-Fluorophenyl)-1-phenylethylamine ½(+)-tartrate mp 213° C. (dec.), (water)

IR (KBr, cm$^{-1}$) 3432, 2900, 1599, 1566, 1512, 1345, 1234, 1067, 825, 701.

$[\alpha]_D^{25} -66.9°$ (c=0.3, methanol).

(+)-2-(4-Fluorophenyl)-1-phenylethylamine ½(−)-tartrate mp 211°–213° C. (dec.), (water).

IR (KBr, cm$^{-1}$) 3432, 2892, 1597, 1564, 1511, 1344, 1233, 1066, 824, 700.

$[\alpha]_D^{25} +69.7°$ (c=0.3, methanol).

Example 1

(±)-1-[1,2-Bis(4-fluorophenyl)]ethyl-4-[2-(3,4-dimethoxyphenyl)ethyl]piperazine dihydrochloride (compound No.1)

(±)-1,2-Bis(4-fluorophenyl)ethylamine (750 mg, prepared by treatment of the hydrochloric acid salt with potassium carbonate), N,N-bis(2-chloroethyl)-2-(3,4-dimethoxyphenyl)ethylamine hydrochloride (738 mg), sodium iodide (965 mg) and potassium carbonate (445 mg) were added to N,N-dimethylformamide (DMF, 18 ml) and the mixture was stirred for 2 hours at 80° C. The reaction mixture was poured into water (150 ml) and extracted with ethyl acetate. The organic layer was washed with saturated sodium chloride solution, dried over anhydrous magnesium sulfate and concentrated in vacuo. The oily residue was purified by silica gel column chromatography. The purified oily product was dissolved in methanol. To the solution, HCl/methanol was added and the solution was concentrated in vacuo. Separated crystals were collected by filtration to give 670 mg (57.9%) of the titled compound.

mp 265°–267° C. (dec.), (methanol—ethanol—ethyl acetate). IR (KBr, cm$^{-1}$) 3368, 2920, 2296, 1601, 1508, 1437, 1258, 1229, 1152, 1019, 835.

Following compounds were prepared by the similar method as in the above.

(±)-1-[1-(4-Fluorophenyl)-2-phenyl]ethyl-4-[2-(3,4-dimethoxyphenyl)ethyl]piperazine dihydrochloride (compound No.2)

mp 263° C. (dec.), (ethanol).

IR (KBr, cm$^{-1}$) 3408, 2980, 2320, 1604, 1515, 1451, 1257, 1147, 1025, 843.

(±)-1-[2-(4-Fluorophenyl)-1-phenyl]ethyl-4-[2-(3,4-dimethoxyphenyl)ethyl]piperazine dihydrochloride (compound No.3)

mp 264° C. (dec.), (ethanol).

IR (KBr, cm$^{-1}$) 3412, 2936, 2320, 1602, 1509, 1453, 1260, 1156, 1023, 759.

(±)-1-[1,2-Bis(4-fluorophenyl)]ethyl-4-[2-[(3,4-methylenedioxy)phenoxy]ethyl]piperazine dihydrochloride (compound No.10)

mp 246°-247° C. (dec.), (ethanol).

IR (KBr, cm$^{-1}$) 3416, 2984, 2324, 1606, 1509, 1489, 1230, 1184, 1035, 841.

Example 2

(−)-1-[1,2-Bis(4-fluorophenyl)]ethyl-4-[2-(3,4-dimethoxyphenyl)ethyl]piperazine dihydrochloride (compound No.11)

To a solution of (−)-1,2-bis(4-fluorophenyl)ethylamine ½(+)-tartrate (950 mg) and N,N-bis(2-chloroethyl)-2-(3,4-dimethoxyphenyl)ethylamine hydrochloride (754 mg) in DMF (40 ml), sodium iodide (989 mg) and potassium carbonate (1764 mg) were added and the mixture was stirred for 2 hours at 80° C. After cooling, ethyl acetate and water were added to the mixture. The organic layer was washed with water and saturated sodium chloride solution, dried over anhydrous magnesium sulfate and concentrated in vacuo. To the oily product dissolved in ethanol, HCl/methanol was added and separated crystals were collected by filtration to give 597 mg (50%) of the titled compound.

mp 266°-267° C. (dec.), (ethanol).

IR (KBr, cm$^{-1}$) 3420, 2940, 2324, 1606, 1515, 1452, 1259, 1150, 1025, 841.

$[\alpha]_D^{25}$ −34.2° (c=0.2, methanol).

Following compounds were prepared by the similar method as in the above.

(+)-1-[1,2-Bis(4-fluorophenyl)]ethyl-4-[2-(3,4-dimethoxyphenyl)ethyl]piperazine dihydrochloride (compound No.12)

mp 266°-267° C. (dec.), (ethanol).

IR (KBr, cm$^{-1}$) 3424, 2980, 2316, 1606, 1510, 1452, 1258, 1148, 1025, 841.

$[\alpha]_D^{25}$ +34.0° (c=0.2, methanol).

(−)-1-[1-(4-Fluorophenyl)-2-phenyl]ethyl-4-[2-(3,4-dimethoxyphenyl)ethyl]piperazine dihydrochloride (compound No.13)

mp 265°-266° C. (dec., (ethanol).

IR (KBr, cm$^{-1}$) 3412, 2984, 2324, 1605, 1517, 1451, 1258, 1148, 1026, 843.

$[\alpha]_D^{25}$ −37.2° (c=0.3 methanol).

(+)-1-[1-(4-Fluorophenyl)-2-phenyl]ethyl-4-[2-(3,4-dimethoxyphenyl)ethyl]piperazine dihydrochloride (compound No.14)

mp 265°-266° C. (dec.), (ethanol).

IR (KBr, cm$^{-1}$) 3416, 2984, 2336, 1606, 1518, 1452, 1258, 1148, 1026, 844.

$[\alpha]_D^{25}$ +39.7° (c=0.3, methanol).

(−)-1-[2-(4-Fluorophenyl)-1-phenyl]ethyl-4-[2-(3,4-dimethoxyphenyl)ethyl]piperazine dihydrochloride (compound No.15)

mp 265°-266° C. (dec.), (ethanol).

IR (KBr, cm$^{-1}$) 3424, 2948, 2324, 1593, 1509, 1450, 1260, 1146, 1030, 761.

$[\alpha]_D^{25}$ −38.7° (c=0.3, methanol)

(+)-1-[2-(4-Fluorophenyl)-1-phenyl]ethyl-4-[2-(3,4-dimethoxyphenyl)ethyl]piperazine dihydrochloride (compound No.16)

mp 264°-266° C. (dec.), (ethanol).

IR (KBr, cm$^{-1}$) 3428, 2944, 2320, 1593, 1512, 1451, 1260, 1145, 1028, 761.

$[\alpha]_D^{25}$ +36.8° (c=0.3, methanol).

FORMULATIONS

The following formulations are illustrative.

A) Tablet

| | |
|---|---|
| compound No. 1 | 5 mg |
| lactose | 74.4 mg |
| starch | 20 mg |
| hydroxypropylcellulose | 4 mg |
| calcium carboxymethylcellulose | 6 mg |
| magnesium stearate | 0.6 mg |
| total | 110 mg |
| compound No. 1 | 30 mg |
| lactose | 49.4 mg |
| starch | 20 mg |
| hydroxypropylcellulose | 4 mg |
| calcium carboxymethylcellulose | 6 mg |
| magnesium stearate | 0.6 mg |
| total | 110 mg |
| compound No. 2 | 10 mg |
| lactose | 78 mg |
| crystalline cellulose | 25 mg |
| low substituted hydroxypropylcellulose | 6 mg |
| magnesium stearate | 1 mg |
| total | 120 mg |
| compound No. 3 | 50 mg |
| lactose | 68 mg |
| crystalline cellulose | 40 mg |
| low substitued hydroxypropylcellulose | 10 mg |
| magnesium stearate | 2 mg |
| total | 170 mg |
| compound No. 4 | 10 mg |
| lactose | 100 mg |
| crystalline cellulose | 40 mg |
| hydroxypropylcellulose | 8 mg |
| low substituted hydroxypropylcellulose | 10 mg |
| magnesium stearate | 2 mg |
| total | 170 mg |

B) Granule

| | |
|---|---|
| compound No. 4 | 30 mg |
| lactose | 145 mg |
| polyvinylpyrrolidone | 15 mg |
| calcium carboxymethylcellulose | 5 mg |
| magnesium stearate | 5 mg |
| total | 200 mg |
| compound No. 11 | 30 mg |
| lactose | 145 mg |
| polyvinyl pyrrolidone | 15 mg |
| calcium carboxymethylcellulose | 5 mg |
| magnesium stearate | 5 mg |
| total | 200 mg |

C) Capsule

| | |
|---|---|
| compound No. 4 | 5 mg |
| lactose | 140 mg |
| magnesium stearate | 5 mg |
| total | 150 mg |

| | |
|---|---|
| compound No. 12 | 30 mg |
| lactose | 145 mg |
| polyvinyl pyrrolidone | 15 mg |
| calcium carboxymethylcellulose | 5 mg |
| magnesium stearate | 5 mg |
| total | 200 mg |

We claim:

1. A compound of the formula or a pharmaceutically acceptable salt thereof,

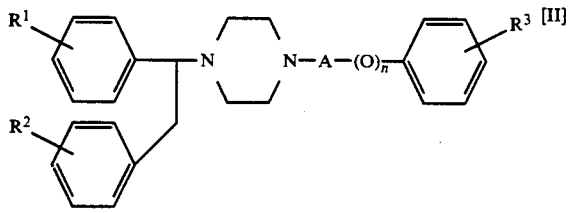

wherein $R^1$ is hydrogen or fluorine;

$R^2$ is hydrogen or fluorine;

$R^3$ is hydrogen, lower alkyl, lower alkoxy, halogen or lower alkylenedioxy;

A is straight or branched lower alkylene having 1 to 6 carbon atoms; and n is 0 or 1, provided that at least one of $R^1$ or $R^2$ is fluorine.

2. The compound as in claim 1 wherein $R^1$ and $R^2$ are fluorine; and $R^3$ is methoxy or methylenedioxy.

3. The compound as in claim 1 wherein $R^1$ is hydrogen;

$R^2$ is fluorine; and $R^3$ is methoxy.

4. The compound as in claim 1 wherein $R^1$ is fluorine;

$R^2$ is hydrogen; and $R^3$ is methoxy.

5. 1-[1,2-Bis(4-fluorophenyl)],ethyl-4-[2-(3,4-dimethoxyphenyl) ethyl]piperazine or a pharmaceutically acceptable salt thereof.

6. 1-[1-(4-Fluorophenyl)-2-phenyl]ethyl-4-[2-(3,4-dimethoxyphenyl)ethyl]piperazine or a pharmaceutically acceptable salt thereof.

7. 1-[2-(4-Fluorophenyl)-1-phenyl]ethyl-4-[2-(3,4-dimethoxyphenyl)ethyl]piperazine or a pharmaceutically acceptable salt thereof.

8. 1-[1,2-Bis(4-fluorophenyl)]ethyl-4-[2-(3,4-methylenedioxy)phenoxy]ethyl]piperazine or a pharmaceutically acceptable salt thereof.

9. A pharmaceutical composition comprising (i) a compound of the formula (II) as defined in claim 1 or a pharmaceutically acceptable salt thereof in an effective amount for treatment of disorders of the cerebro-neural transmission system and (ii) at least one pharmaceutically acceptable excipient.

10. The compound as in claim 1 wherein said $R^3$ is selected from the group consisting of hydrogen; a lower alkyl selected from the group consisting of methyl, ethyl, propyl, isopropyl, butyl and hexyl; a lower alkoxy selected from the group consisting of methoxy, ethoxy, propoxy, isopropoxy, butoxy and hexyloxy; a halogen selected from the group consisting of fluorine, chlorine, bromine and iodine; and a lower alkylenedioxy selected from the group consisting of methylenedioxy and ethylenedioxy; and said salt is selected from the group consisting of a hydroxychloric acid salt, a sulfonic acid salt, a lactic acid salt, a maleic acid salt and an oxalic acid salt.

11. The composition as in claim 9 wherein the compound is selected from the group consisting of 1-(1,2-bis(4-fluorophenyl)ethyl-4-(2-(3,4-dimethoxyphenyl)-ethyl)piperazine, 1-(1-4-fluorophenyl)-2-phenyl-4-(2-(3,4-dimethoxyphenyl)ethyl)piperazine, 1-(2-(4-fluorophenyl)-1-phenyl)ethyl-4-(2-(3,4-dimethoxyphenyl)ethyl)piperazine and 1-(1,2-bis(4-fluorophenyl)ethyl-4-(2-3,4-methylenedioxy)phenoxyethyl)piperazine.

12. The composition as in claim 9 wherein said amount is effective for the treatment of defects of memory, insomnia, depression, schizophrenia or dementia which are disorders of the cerebro-neural transmission system.

13. The composition as in claim 9 wherein the amount of said compound is an effective serotonine antagonist effective amount.

14. The compound as in claim 2, wherein n is zero.

15. The compound as in claim 3, wherein n is zero.

16. The compound as in claim 4, wherein n is zero.

17. The compound as in claim 2, wherein A is a straight $C_2$ alkylene.

18. The compound as in claim 3, wherein A is a straight $C_2$ alkylene.

19. The compound as in claim 4, wherein A is a straight $C_2$ alkylene.

* * * * *

UNITED STATES PATENT AND TRADEMARK OFFICE
CERTIFICATE OF CORRECTION

PATENT NO. : 5,153,198

DATED : October 6, 1992

INVENTOR(S) : Takakazu MORITA et al

It is certified that error appears in the above-identified patent and that said Letters Patent is hereby corrected as shown below:

Column 1, line 7, "Ser. No. '07/486,521" should be
--Ser. No. 07/486,542--.

Column 1, line 8, after "U.S. Pat. No. 5,087,627" insert
--, issued February 11, 1992--.

Signed and Sealed this

Sixth Day of September, 1994

Attest:

BRUCE LEHMAN

*Attesting Officer*   *Commissioner of Patents and Trademarks*